United States Patent [19]

Spielvogel et al.

[11] Patent Number: 4,806,430

[45] Date of Patent: Feb. 21, 1989

[54] FILM-FORMING SILICONE COMPOSITIONS HAVING LUBRICATING PROPERTIES

[75] Inventors: David E. Spielvogel, Springboro; Richard J. Zdrahala, Dayton, both of Ohio

[73] Assignee: Becton, Dickinson and Company, Franklin Lakes, N.J.

[21] Appl. No.: 120,901

[22] Filed: Nov. 16, 1987

Related U.S. Application Data

[62] Division of Ser. No. 804,209, Dec. 3, 1985, Pat. No. 4,720,521.

[51] Int. Cl.$^4$ ............................................. B32B 9/06
[52] U.S. Cl. .................................. 428/450; 30/346.5; 206/571; 604/187; 524/862; 524/588; 524/731; 528/15; 528/31; 528/32; 427/387; 428/447; 525/478
[58] Field of Search ............... 30/346.5; 206/571; 604/187; 534/862; 528/15, 31, 32; 524/588, 731; 427/387; 428/447, 450; 525/478

[56] References Cited

U.S. PATENT DOCUMENTS

| | | | |
|---|---|---|---|
| 3,957,713 | 5/1976 | Jeram et al. | 524/779 |
| 4,539,357 | 9/1985 | Bobear | 528/15 |
| 4,621,029 | 11/1986 | Kawaguchi | 528/31 |
| 4,720,521 | 1/1988 | Spielvogel et al. | 524/862 |

*Primary Examiner*—Melvyn I. Marquis
*Attorney, Agent, or Firm*—Richard E. Brown

[57] ABSTRACT

A film-forming siloxane composition having excellent adherent and lubricating properties comprising a reactive component having a combination of three siloxane polymers chemically crosslinked, and a non-reactive component dispersed therein. Substrates are dipped or otherwise coated with the compositions, at which time they are cured quickly under heat to a durable, adherent lubricating surface which is dry to the touch. Of particular advantage is the use of these films on hypodermic needles, razor blades, catheters and the like.

9 Claims, 1 Drawing Sheet

METAL SUBSTRATE

FILM-FORMING SILICONE COMPOSITIONS HAVING LUBRICATING PROPERTIES

This is a division of application Ser. No. 804,209, filed Dec. 3, 1985, now U.S. Pat. No. 4,720,521.

BACKGROUND OF THE INVENTION

The instant invention relates to a film-forming silicone composition having a non-reactive lubricating component dispersed or distributed within a reactive component such that when the composition is applied to or used in conjunction with a substrate surface, it coats and adheres to the surface while providing surface lubrication.

Certain silicone coating compounds are well known in the art for their lubricating properties. Those compounds disclosed have various disadvantages and shortcomings which the inventive compositions seek to overcome. U.S. Pat. No. 4,573,073 discloses the use of cured organosilioxane copolymers on fine cutting edges such as razor blades and hypodermic needles. The copolymers of this reference consist of:

(1) 5 to 20 weight percent of polymeric units of the formula:

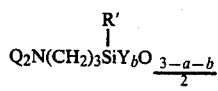

Wherein B is an alkyl radical $C_{1-6}$; Y is —OH and OR' where R' is an alkyl radical up to 3 carbons; Q is —$CH_3$ or —$CH_2CH_2NH_2$; a and b have a value of 0 or 1 where their sum is from 0 to 1; and (2) 80 to 95 weight percent of polymeric units of the formula

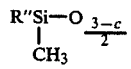

wherein R" is —OH or —$CH_3$ radicals and c has a value of 1 or 2.

The coatings of this reference suffer several shortcomings and disadvantages. To begin with, these polymers are moisture cured. Although some lubricating effect is obtained while these films are in the uncured state, it takes from two to ten days to obtain a fully cured coating. The polymers of this reference are amine termianted, thus the surfaces of this polymer due to the amine functionality are alkaline in nature. This alkalinity may potentially initiate a hemolytic and/or thrombogenic reaction when used in articles which contact blood.

Another known silicone lubricant widely used in the biomedical field on hypodermic needles is polycimethylsiloxane (PDMS). While the medical grade fluids have the advantage of being chemically inert, these materials have a tendency to creep or migrate from the surface to which they are applied. For example, in the case of a hypodermic needle coated with PDMS, the coating might be substantially removed due to frictional forces during penetration of the skin and vein, making subsequent removal of the needle difficult and painful to the patient. Migration during storage and inadvertant removal during processing is also a concern.

Heretofore, the prior art has not disclosed a lubricating siloxane composition which cures quickly to an adherent film, without migration problems or long cure times. It is apparent that a need exists for a lubricating composition which when applied to substrate surfaces such as hypodermic needles, cutting edges, razor blades and the like, adheres to the substrate surface and provides lubrication, durability and biocompatibility. In the case of hypodermic needles, the lubricating composition serves to decrease the penetration force into the skin or vein, as well as decrease the drag and retract force during removal.

SUMMARY OF THE INVENTION

The instant invention relates to a film-forming composition comprising:

(a) a reactive component comprising of a first siloxane polymer having two or more vinyl groups; a second siloxane crosslinking polymer having two or more pendent hydrogen groups; and a third siloxane chain-extending polymer having two or more terminal hydrogen groups; and (b) a non-reactive lubricating component comprising a siloxane polymer dispersed within said reactive component.

The reactive component is a chemically crosslinked, surface adherent polydimethylsiloxane, which serves as a matrix for the non-reactive component dispersed therein. Each of the three siloxane polymers of the reactive component is required to achieve the durability and adherent properties required for the intended usefulness of the compositions as a film or coating. Preferably a mixture of polymers is used for each of the three types of required polymers in the reactive component. For example, a mixture of vinyl terminated or vinyl pendent siloxane polymers can be used as the first siloxane; a mixture of polymers having at least two pendent hydrogen groups can be used as the second polymer; and a mixture of chain-extending polymers having terminal hydrogen groups can be used as the third siloxane polymer.

BRIEF DESCRIPTION OF THE DRAWINGS

The FIGURE is a diagramatic illustration of the probable chemical configuration of the cured film of the invention on a substrate.

DETAILED DESCRIPTION OF THE INVENTION

Figure 1:
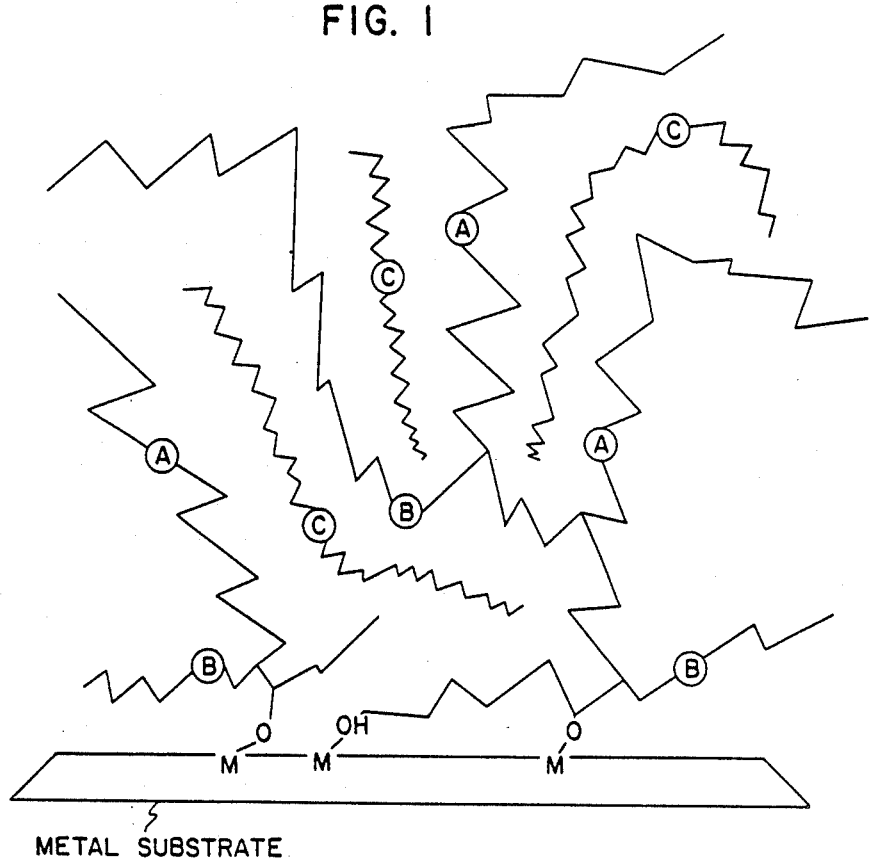

The First Siloxane Polymer of the Reactive Component

The first siloxane polymer of the reactive component is present in amounts of about 3% to about 35% by weight of the total film-forming composition; and preferably in amounts of about 10% to about 30% weight percent. This polymer corresponds to the following structural formulae:

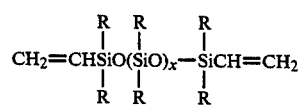

OR

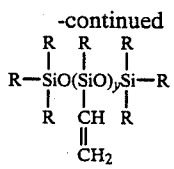

wherein R is alkyl $C_{1-20}$, haloalkyl, aryl, haloaryl, cycloalkyl, silacyclopentyl, aralkyl and mixtures thereof; x is about 60 to about 1000, and preferably about 200 to about 320; and y is about 3 to about 25. Copolymers and mixtures of these polymers are also contemplated.

It is preferred that a mixyture of siloxane polymers selected from the formulae I and/or II be used in the reactive component. Most preferably this mixture comprises a mixture of two different molecular weight vinyldimethylsilyl terminated polydimethylsiloxane polymers, wherein one of the polymers has an average moleculare weight of about 5,000 to about 25,000 and preferably about 16,000, and the other polymer has an average molecular weight of about 30,000 to about 75,000 and preferably about 38,000. The lower molecular weight siloxane is generally present in amounts of about 20% to about 80%, and preferably about 60% by weight of this mixture; and the higher molecular weight siloxane is present in amounts of about 80% to about 20%, and preferably about 40% by weight of this mixture.

The Second Siloxane Polymer of the Reactive Component

The second siloxane polymer of the reactive component is present in amounts of about 0.3 to about 5.5% by weight of the total composition and preferably in amounts of about 0.5 to about 4.0%, and comprises:

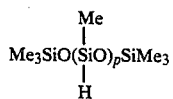

wherein p is about 8 to about 12 and preferably about 10.

The Third Siloxane Polymer of the Reactive Component

The final requirement of the reactive component is a siloxane chain-extending polymer having two or more terminal hydrogen groups. These compounds correspond to the formula IV below and are generally present in the reactive component in amounts of about 2.5% to about 50%, and preferably about 5% to about 40% by weight of the reactive component.

wherein p is about 140 to about 170 and preferably about 150 to about 160.

Preferably a mixture of these polymers is also used comprising two different moledular weight materials. For example, a preferred embodiment incorporates about 2% to about 5% by weight of the mixture of a trimethyl asilyl terminated polymethylhydrogensiloxane having an average molecular weight of about 400 to about 7,500, and preferably about 1900, in admixture with about 98% to about 95% of a dimethylhydrogen silyl-terminated polymethylhydrogensiloxane having an average molecular weight of about 400 to about 37,000 and preferably about 12,000.

The three required siloxane polymers of the reactive component are present in relative weight ratios of about 0:2:5:1 to about 2:20:1 and preferably about 0.4:4:1 to about 1.5:16:1. In these ratios, an adherent, fast curing film is obtained with the added advantage that it is optically clear and free of cloudiness or opaque appearance.

The reactive component has a viscosity ranging from about 100 to about 100,000 centistokes and an average molecular weight per crosslink of about 5,000 to about 75,000. The mole ratio of vinyl groups to hydrogen groups in the reactive component is about 0.010:1 to about 0.20:1. The mole ratio of hydrogen groups of the crosslinking polymer to hydrogen groups of the chain-extending polymer is about 5.0:1 to about 20:1.

Non-Reactive Component

The non-reactive component of the inventive compositions is responsible for the lubricating properties of the resultant films and coatings. This component comprises a siloxane polymer having an average moleculare weight of about 1900 to about 100,000, and preferably about 5,000 to about 100,000. Generally, this corresponds with a viscosity of about 20 to about 300,000 centistokes (cstks). The non-reactive component is present in amounts of about 10% to about 90%, and preferably about 70% to about 805 by weight of the total composition.

The non-reactive component generally corresponds to compounds of formula V:

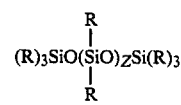

wherein R is alkyl $C_{1-20}$, haloalkyl, aryl, haloaryl, cycloalkyl, silacyclopentyl, aralkyl and mixtures thereof; and Z is about 20 to about 1,800. Preferably, the non-reactive component has the following formula:

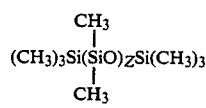

wherein Z is about 70 to about 1800 and preferably about 70 to about 1,350.

The non-reactive polymer viscosity and the weight ratio of the non-reactive component to the reactive component are the two most significantly variables influencing the properties of the final coatings and films. When applied to a hypodermic needle as a coating, the penetration, drag, retract and adhesion to needle-surface are affected by these variables. Generally, the lower viscosity compositions cure to better lubricating films and coatings. Additionally, better lubricating properties are also obtained in the resultant films and coatings if the weight ratio of the non-reactive lubricating component to reactive component is increased. Penetration forces are lowest when the ratio of the crosslinker (the second siloxane polymer of the reactive component) to the chain extender is lowest. The weight ratio of the reactive component to the non-reactive component is preferably about 20:80 to about 30:70.

The inventive compositions are useful on a variety of materials and substrates such as metal and plastics and in applications where dry lubrication is required. The inventive compositions have excellent adherent properties when cured and if used in the proper thickness may serve as relatively permanent lubricative films.

Curing of the reactive portion can be accomplished by conventional methods well known in the art. For example, heat curing via oven or radio frequency (RF) are useful methods as well as the use of gamma radiation. Any mechanism which will initiate the hydrosilylation reaction is a useful curing technique. In the case of oven curing, temperatures should range from about 150° to about 180° C. and residence time in the oven is generally about 30 to about 40 seconds, depending on the precise formulation. If RF techniques are used, the coil should conduct enough heat to obtain a substrate surface temperature of about 180° to about 240° C. At these temperatures, only about 2 to about 4 seconds are required for cure. This technique is particularly useful on hypodermic needles, catheters and cutting edges where production costs can be lowered significantly. If gamma radiation techniques are used, the need for hydrosilylation initiating catalyst is eliminated, since the radiation will start the cure. This technique has the advantage of sterilizing as well, which is useful in medical applications.

The inventive compositions can be partially cured to attach them to the substrate, and then fully cured at a later time. For exmaple, air drying will permit partial cure. The compositions are initially fluid and can be applied directly to the substrate in any suitable manner for example by dipping, brushing or spraying. The exact thickness of the coating does not appear to be critical and very thin coatings, e.g., one or two microns exhibit effective lubricating properties. While not necessary for operability, it is desirable that the thickness of the coating be substantially uniform throughout.

The inventive compositions can be applied from an inert, solvent carrier, such as non-toxic chlorinated or fluorinated hydrocarbons. For example, 1,1,2-trichloro-1,2,2-trifluoroethane, freon and the like are useful. Conventional hydrocarbon solvents such as alkanes, toluene, petroleum ether and the like are also useful in applications where toxiciology is not considered important.

The compositions when cured have two distinct properties which are related to the two distinct components. The reactive component gives the cured product its surface adherent properties, allowing the film to coat and stick to the substrate. Chemical attraction of the hydrogen functionality on the crosslinked film to the oxides and hydroxyl groups on the substrate surface are believed to be primarily responsible for the adhesion, although some physical adhesion may also be occurring. The adhesion thus provides a definite advantage in that they do not wipe off and remain on the substrate without creep or migration over long periods of storage time. The films are dry to the touch and are less likely to trap dust and dirt as the prior art compositions.

As previously stated, the non-reactive component provides the lubricating property to the film. Lubrication is experienced on the non-adherent surface fo the film, that is, on the exposed side. Without wising to be bound to any one theory, the non-reactive polymer chains are believed to fit within the voids of the cured reactive component. FIG. 1 provides an illustration of the probable chemical configuration of the cured film on a substrate. Chains labelled "A" represent the siloxanes of the reactive component having vinyl functionality. Those labelled "B" represent siloxanes of the reactive component having hydrogen functionality. The substrate is depicted as a metal surface where metal oxides (MO) and metal hydroxyl grups (MOH) are present. Chemical bonds can be seen between the functional groups of the substrate. The chains labelled "C" represent the non-reactive component, which can be seen to be physically entrapped within the voids of the reactive chains.

To prepare the inventive compositions, appropriate quantities of the three siloxanes required for the reactive component are mixed along with a catalyst solution. It is preferred that the vinyldimethylsilyl terminated PDMS polymers be mixed together first, followed by addition of the catalyst and finally the second and third siloxane, e.g., the cross-linker and chain-extender. Mixing takes place for five to fifteen minutes at room temperature. This reactive portion is then combined with the non-reactive polymer and mixed for about five minutes at room temperature. The mixture is then diluted with a solvent, for example 1,1,2-trichloro-1,2,2-trifluoroethane to prepare a 4 weight % solids concentration. The fluid mixture is then ready to be applied to a substrate by one of the aforementioned techniques, and subsequently cured to a film.

The films and coatings of the instant invention have an average moleculare weight per crosslink of about 5,000 to about 110,000 and preferably about 15,000 to about 37,000.

The most preferred composition of the instant invention is a composition containing the following siloxane polymers:

Reactive Component

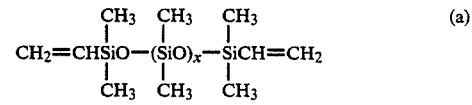 (a)

wherien x is about 200 to about 500;

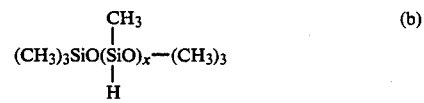 (b)

wherein x is about 8 to about 12;

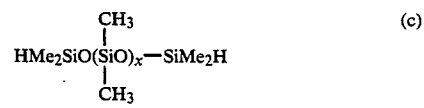 (c)

wherein x is about 160; and

Non-reactive Component

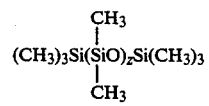

wherein z is about 70 to about 1,350.

This preferred composition has been found to be especially useful and effective in coating hypodermic needles.

The following examples serve to provide further appreciation of the invention but are not meant in any way to restrict the effective scope of the invention. All percentages are by weight of the total composition unless otherwise specified.

EXAMPLE 1

This example is intended to show the criticality of process conditions and materials used in the preparation of the coating formulations. Six formulations were prepared according to the procedure below and needles were coated therefrom. All of the formulations in Table I were prepared according to the following procedure.

A homogenous solution of the inylidimethylsilyl terminated polydimethylsiloxane polymers were prepared by mixing 1,000 centistoke and 10,000 centistoke polymers for 3–5 minutes. To this solution was added chloroplatinic acid catalyst in a sufficient amount ot catalyze the silane to vinylsilane addition reaction, and the solution was mixed for about 3–5 minutes. a separate homogenous solution of the crosslinker and chain-extender was prepared at room temperature by mixing for 3–5 minutes. The vinyl functional polymer solution was added to the crosslinker/chain-extender solution (hydrogen functional solution) and mixed for 3–5 minutes. To this reactive polymer solution was added the non-reactive silicone polymer and the combined sample is mixed for 3–5 minutes at room temperature. Samples of the inventive coating compositions were diluted with 1,1,2-trichloro1,2,2-trifluoroethane to a concentration of 4 wt. % solids.

TABLE I

COATING FORMULATIONS (weight %)

| Ingredients | A | B | C | D | E | F |
|---|---|---|---|---|---|---|
| A. Reactive Component | | | | | | |
| ViMe$_2$ Siloxane Polymer[1] | 4.5 | 10.8 | 8.4 | 21 | 1.2 | 14 |
| ViMe$_2$ Siloxane Polymer[2] | 10.5 | 7.2 | 3.6 | 9 | 1.8 | 21 |
| Crosslinker[3] | 1.75 | 1.5 | .9 | 1.5 | .875 | .75 |
| Chain-extender[4] | 33.25 | 10.5 | 17.1 | 18.5 | 6.125 | 14.25 |
| B. Non-Reactive Component | | | | | | |
| Weight % | 50 | 70 | 70 | 50 | 90 | 50 |
| Lubricative Polymer/ Viscosity[5] | 350 | 350 | 1000 | 12,500 | 12,500 | 110,000 |

[1]ViMe$_2$ Siloxane Polymer: 1,000 centistokess (cstks.)
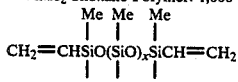

[2]ViMe$_2$ Siloxane Polymer: 10,000 cstks.
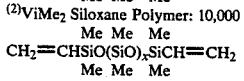

[3]Crosslinker: Me$_3$SiO(SiO)$_x$SiMe$_3$, 25 cstks.
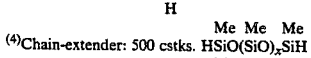

[4]Chain-extender: 500 cstks. HSiO(SiO)$_x$SiH
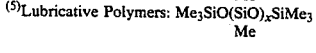

[5]Lubricative Polymers: Me$_3$SiO(SiO)$_x$SiMe$_3$

EXAMPLE 2

This example is intended to demonstrate by comparative tests the advantages the inventive compositions have over the prior art. The tests were specifically designed to compare the lubrication properties of the inventive compositions against the prior art.

Each of the compositions in Table I was used as a coating material for clean stainless steel, 16 gauge hypodermic needles. Five needle samples were used for each composition. The needles coated with the inventive compositions (A–F) were mechanically dipped 19 mm (¾") deep and withdrawn at a rate of about 12 mm/sec. The comparative compositions of the prior art (G–H) were similarly dipped and withdrawn at the rate of about 6 mm/sec. Certain of the control needles were dipped 19 mm (¾") deep in 4 wt % solution of the commercial version of the composition described in the aforementioned U.S. Pat. No. 3,574,673. Other control needles were dipped similarily in a 4 wt % solution of 12,500 centistoke Dow Corning 360 Fluid. The control polymer solutions all used 1,1,2-trichloro-1,2,2-trifluoroethane as the solvent.

Coating of all the needles was done using a machine which controlled the rate of dipping and withdrawal. The thickness of the coating is related to the speed of withdrawal of the substrate. In the case of needles, an optimum speed for obtaining acoating with the highest degree of lubricity was chosen through routine experimentation and experimental modeling. Generally, the faster the substrate is withdrawn from the fluid composition, the thicker the resultant coating. This would be expected since there would be less time for the fluid to run off the substrate.

Speeds of withdrawal for all formulations tested were chosen to maximize the degree of lubricity. The speeds for the control formulations were the conventional rates used for high speed assembly-line coating. The speeds for maximizing lubricity of the inventive compositions was determined to about about 12.7 mm/sec; and was about 6.35 mm/sec for the control composition. Thus, the respective rates were previously determined by routine experimentation to be the appropriate ones for obtaining a coating with the highest degree of lubricity.

The coated needles were then tested for penetraiton, drag, retract and catheter/needle adhesion. A natural isoprene rubber, ASTM D-2000 type AA was used a a test membrane through which the needles were pierced. The force required for the 16 gauge needles to pierce a 1/16"×1×1⅛ membrane was recorded as the penetration value. The membrane was held by a clamp assembly at a 45° angle and the penetration and withdrawal was performed by a Model 1122 Instron Tensile machine. A fresh, unpierced membrane was used for each measurement.

For purposes of this invention, the drag force is defined as the force required to glide the needle surface through the puntured membrane when inserting th needle through the membrane. That is, it is the functional force between the needle and the membrane after the needle has punctured the membrane and is continued to be moved in relation to the membrane.

The retract force is the force required to slide the needle surface through the membrane when withdrawing the needle.

The catheter/needle adhesion force is the force required to separate the catheter from the needle at their point of adhesion.

Turning to Table II, it is clear that the inventive compositions A–F demonstrated siginficantly lower values for the force required to penetrate the skin, drag through the skin and for retraction, than the two commercially available silicone lubricants shown. The values for catheter/needle adhesion indicated acceptable lubricating properties such that the needle can be easily separated from the catheter when the needle is withdrawn from the catheter to needle assembly. It is apparent that the inventive compositions have excellent adherent properties on the substrate to which they are applied, yet are non-tacky and do not transfer to adjacent surfaces. Rather, these adjacent surfaces easily slide over the coated surface due to the lubricating properties of the inventive compositions. The inventive compositions may be employed as coating on a variety of materials and substrates, thereby imparting their lubricating effects. It is apparent that the inventive compositions exhibit improved lubricity over the prior art.

TABLE II

| Needles Coated with Coating: | Penetration | Draq | Retract | Catheter/Needle Adhesion |
|---|---|---|---|---|
| A | 242 | 37 | 37 | 120 |
| B | 257 | 44 | 41 | 95 |
| C | 246 | 18 | 22 | 57 |
| D | 270 | 45 | 44 | 158 |
| E | 288 | 20 | 41 | 70 |
| F | 262 | 56 | 56 | 97 |
| G* | 282 | 76 | 82 | 189 |
| H** | 297 | 29 | 48 | 114 |

*Comparative Composition from U.S. Pat. No. 3,574,073 (Dow Corning MDX-4-4159 commercial needle lubricant)
**Trimethylsilyl terminated PDMS (Dow Corning medical grade 360 fluid silicone)

The invention being thus described, it will be obvious that the same may be varied in many ways. Such variations are not to be regarded as a departure from the spirit and scope of the invention an all such modifications are intended to be included within the scope of the claims.

We claim:

1. An article comprising a substrate having a composition coated onto a surface thereof, said composition adhering to said surface and lubricating said surface, said composition comprising:
   (a) a reactive component for providing adhesion, said reactive component comprising
      (1) a first siloxane polymer having the formula selected from the group consisting of

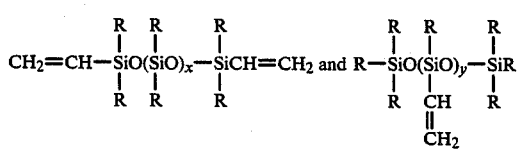

wherein R is selected from the group consisting of alkyl $C_{1-20}$, haloalkyl, aryl, haloaryl, cycloalkyl, silacyclopentyl, aralkyl and mixtures thereof; x is about 60 to about 1000; and y is about 3 to about 25;
      (2) a second siloxane crosslinking polymer of the formula

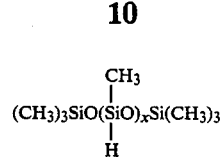

wherein x is about 8 to about 12; and
      (3) a third siloxane chain-extending polymer having the formula

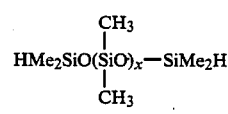

wherein x is about 140 to about 160;
   (b) a non-reactive lubricating siloxane polymer component of the formula

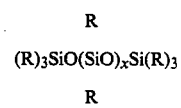

wherein R is selected from the group consisting of alkyl $C_{1-20}$, haloalkyl, aryl, haloaryl, cycloalkyl, silacyclopentyl, aralykl, and mixtures thereof; x is about 20 to about 1350; and
   (c) the mole ratio of vinyl groups to hydrogen groups is within the range of between about 0.010:1 and 0.20:1.

2. The article of claim 1 wherein the substrate surface is metal or plastic.

3. The article of claim 2 wherein the metal surface has a fine cutting edge.

4. The article of claim 1 which is a hypodermic needle.

5. The article of claim 1 which is a razor blade.

6. The article of claim 1 wherein the first siloxane polymer comprises a mixture of two vinyldimethylsilyl terminated polydimethylsiloxanes having respective average molecular weights of about 16,000 and 38,000; the second siloxane polymer has an average molecular weight of about 1900; and the non-reactive lubricating siloxane comprises a trimethylsilyl termianted polydimethylsiloxane having an average molecular weight of about 16,000.

7. The article of claim 1 wherein the weight ratio of reactive component to non-reactive component is about 20:80 to about 30:70.

8. The article of claim 1 wherein the weight ratio of the first siloxane polymer to the second polymer in the reactive mixture is about 30:70 to about 40:60.

9. The article of claim 1 wherein said substrate is plastic and which is a catheter.

* * * * *